(12) United States Patent
Assouline et al.

(10) Patent No.: US 10,380,539 B2
(45) Date of Patent: Aug. 13, 2019

(54) SYSTEMS AND METHODS OF MANAGING INVENTORY IN A MEDICAL FACILITY

(71) Applicants: Jonathan Assouline, Montreal (CA); Anders Larsson, Copenhagen (DK); Richard Philippe, Laval (CA); Jean-Philippe Racette, Piedmont (CA)

(72) Inventors: Jonathan Assouline, Montreal (CA); Anders Larsson, Copenhagen (DK); Richard Philippe, Laval (CA); Jean-Philippe Racette, Piedmont (CA)

(73) Assignee: LOGI D INC., Laval, QC (CA)

( * ) Notice: Subject to any disclaimer, the term of this patent is extended or adjusted under 35 U.S.C. 154(b) by 0 days.

(21) Appl. No.: 13/953,787

(22) Filed: Jul. 30, 2013

(65) Prior Publication Data

US 2014/0027510 A1    Jan. 30, 2014

Related U.S. Application Data

(60) Provisional application No. 61/677,283, filed on Jul. 30, 2012.

(51) Int. Cl.
*G06Q 10/08* (2012.01)
*G06Q 50/22* (2018.01)

(52) U.S. Cl.
CPC .......... *G06Q 10/087* (2013.01); *G06Q 50/22* (2013.01)

(58) Field of Classification Search
CPC ................. G06Q 10/087; G06Q 50/22; G06K 2017/0051; G06K 7/10178
USPC ...................................................... 340/10.2
See application file for complete search history.

(56) References Cited

U.S. PATENT DOCUMENTS

| | | | | |
|---|---|---|---|---|
| 7,516,890 B1* | 4/2009 | Spremo | ................ | G06Q 10/087 235/385 |
| 7,757,947 B2 | 7/2010 | Reznik et al. | | |
| 2002/0111819 A1* | 8/2002 | Li et al. | ........................... | 705/1 |
| 2007/0023512 A1* | 2/2007 | Miller | .................. | G06Q 10/087 235/385 |
| 2010/0042097 A1* | 2/2010 | Newton et al. | ................. | 606/41 |
| 2010/0123559 A1* | 5/2010 | Wilkinson | ........... | G06K 7/0008 340/10.4 |

(Continued)

OTHER PUBLICATIONS

European Search Report, 13826095.5-1955 / 2880604 PCT/CA2013000676, Assouline, Jonathan et al, dated Feb. 16, 2016, 7 pages.

(Continued)

*Primary Examiner* — Sonji N Johnson

(57) ABSTRACT

A inventory information system having an inventory station having an array of unique locations defined thereon; a plurality of indicators, each of the indicators being associated with each of the locations; a plurality of tags, each of the tags having an identifier associated therewith; at least one detector operable to obtain identifier associated with one of the tags when the tag is positioned at one of the locations; and a processor operatively coupled to the at least one detector and the plurality of indicators. The processor is configured to receive the identifier and to determine an inventory status of at least one product associated with the identifier, and operate the indicator associated the location where the tag based upon the inventory status to provide information about the inventory status.

31 Claims, 8 Drawing Sheets

(56) References Cited

U.S. PATENT DOCUMENTS

2011/0202170 A1\* 8/2011 Dawes .................... F25D 29/00
   700/215
2012/0293307 A1\* 11/2012 Djuric et al. ................ 340/10.2

OTHER PUBLICATIONS

PCT International Searching Authority, International Search Report and Written Opinion for PCT Patent Application Serial No. PCT/CA2013/000676, dated Nov. 13, 2013.
Communication pursuant to Article 94(3) EPC, European Patent Office, for European Patent Application Serial No. 13826095.5 dated Oct. 25, 2017.

\* cited by examiner

SYSTEMS AND METHODS OF MANAGING INVENTORY IN A MEDICAL FACILITY

RELATED APPLICATIONS

This application claims the benefit of U.S. Provisional Patent Application No. 61/677,283 filed Jul. 30, 2013, the entire contents of which are hereby incorporated by reference herein for all purposes.

TECHNICAL FIELD

The embodiments described herein relate in general to inventory systems, and more particularly to systems and methods, for providing information about inventory levels in a medical facility.

INTRODUCTION

In various medical institutions, such as hospitals or clinics, there is a large number of products that are being stored on location for use by hospital staff and patients. The products, for example, may include various consumable medical products such as sterilizing agents, bandages, medicaments, surgical equipment and so on. In many cases, the stock levels of the products are monitored so that shortages of the products can be avoided.

Many medical institutions employ inventory systems to help monitor the current inventory levels in the institutions. However, implementing inventory systems may be challenging for a number of reasons. For example, many hospital store rooms or inventory location may be accessed by a large number of staff working at the hospital, and it may be difficult to train all the staff members that have access to the inventory location to use the inventory system in a desired manner.

In many cases, the staff in a medical setting may not be familiar with how to use the inventory system and they may therefore misuse or bypass the use of the inventory system. Having dedicated inventory staff to monitor the inventory stock levels at each location when the products are stored may help mitigate this problem but is generally not efficient or cost effective.

SUMMARY

In some aspects, there is provided an inventory information system having an inventory station with an array of unique locations and a plurality of indicators. Each of the indicators is associated with at least one of the locations. The inventory system also includes a plurality of tags, each of the tags having an identifier associated therewith, at least one detector operable to obtain an identifier associated with one of the tags when the tag is positioned at one of the locations, and a processor operatively coupled to the at least one detector and the plurality of indicators. The processor is configured to receive the identifier and to determine an inventory status of at least one product associated with the identifier, and operate the indicator associated with the location where the tag based upon the inventory status to provide information about the inventory status.

According some aspects, each of the indicators is uniquely associated with each of the locations.

The at least one detector may include at least one radio frequency identification (RFID) detector, which could be a plurality of RFID detectors, each being associated with each of the locations and positioned proximate thereto.

According to some aspects, the technical specification of each of the detectors may be selected such that tags placed in locations other than the location associated with the detector are not detected by the detector.

According to some aspects, the system may includes detection inhibitors configured to prevent the detectors from detecting tags placed in locations other than the location associated with the detector.

The at least one detector may include at least one directional RFID indicator associated with a plurality of locations, the directional detector operable to detect at least one of the tags placed at one of the associated locations and determine which of the associated locations that the tag is placed at.

At least one of the indicators may include a visual indicator, which may include a light emitting device operable to emit different colour lights, each of the colours of light being associated with a particular inventory status.

At least one of the indicators may include an audio indicator.

According to some aspects, the system may includes at least one display coupled to the at least one processor, the at least one processor configured to provide inventory information using the at least one display.

The system may include at least one communication device coupled to the at least one processor, the at least one communication device operable to communicate with at least one other processor that is remote from the at least one processor to provide and receive inventory information.

According to some other aspects, there is provided a method for providing inventory information. The method includes using a detector associated with a location to obtain an identifier associated with a tag when the tag is placed at the location, determining an inventory status associated with the identifier, and operating an indicator associated with the location to provide inventory information based upon the inventory status.

BRIEF DESCRIPTION OF THE DRAWINGS

Some embodiments will now be described, by way of example only, with reference to the following drawings, in which.

DESCRIPTION OF SOME EMBODIMENTS

Figure 1:
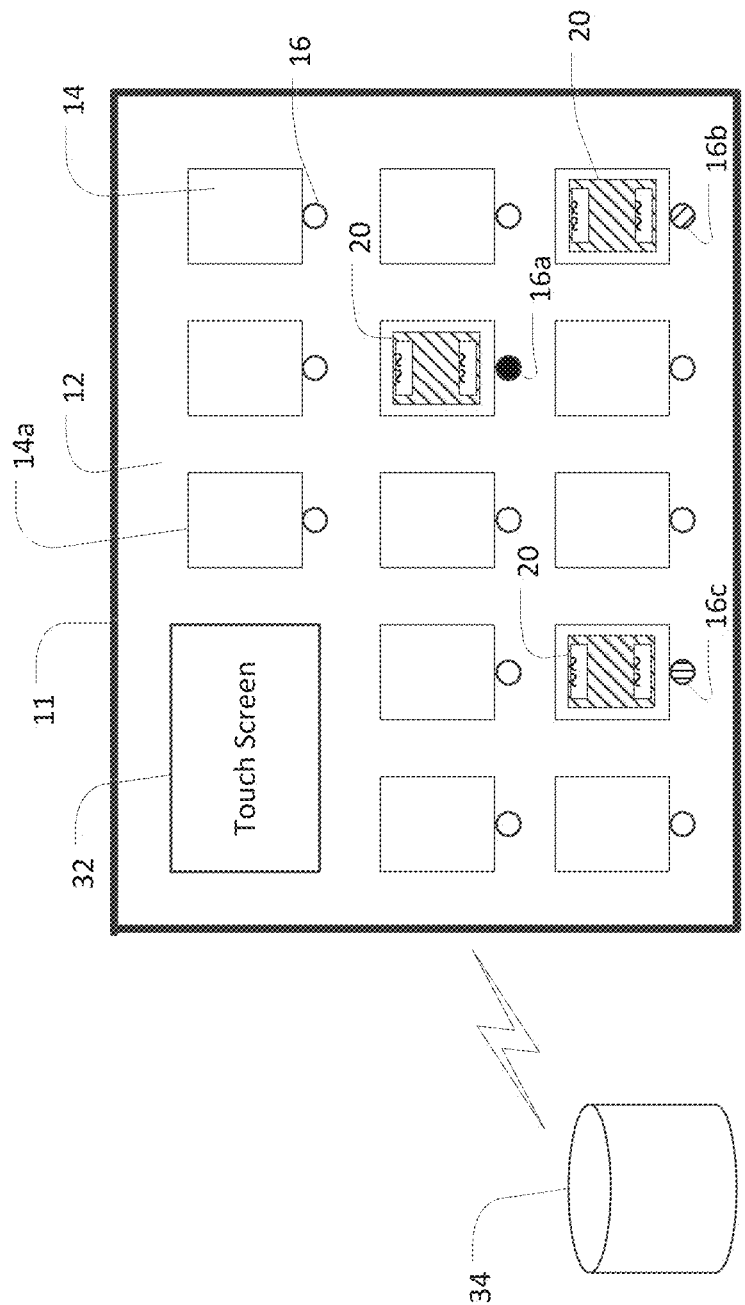
FIG. 1 is a schematic diagram illustrating an inventory system according to some embodiments.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments generally described herein.

Furthermore, this description is not to be considered as limiting the scope of the embodiments described herein in any way, but rather as merely describing the implementation of various embodiments.

In some cases, the embodiments of the systems and methods described herein may be implemented in hardware or software, or a combination of both. In some cases, embodiments may be implemented in one or more computer programs executing on one or more programmable computing devices comprising at least one processor, a data storage device (including in some cases volatile and non-volatile memory and/or data storage elements), at least one input device, and at least one output device.

In some embodiments, each program may be implemented in a high level procedural or object oriented programming and/or scripting language to communicate with a computer system. However, the programs can be implemented in assembly or machine language, if desired. In any case, the language may be a compiled or interpreted language.

In some embodiments, the systems and methods as described herein may also be implemented as a non-transitory computer-readable storage medium configured with a computer program, wherein the storage medium so configured causes a computer to operate in a specific and predefined manner to perform at least some of the functions as described herein.

Referring now to FIG. 1, illustrated therein is a system 10 for managing inventory according to some embodiments, particularly for use in a medical facility. The system 10 includes an inventory station 11. The inventory station 11 includes a substrate 12 which may be a board made of various suitable materials including wood, plastic, metal, etc. In some cases, the inventory station 11 may be wall mounted, shelf mounted, or otherwise installed in a vertical position such that it normally does not take up a large amount of floorspace.

The inventory station 11 has a plurality of locations 14 defined thereon. Each of the locations may be discrete in that the locations 14 generally do not overlap. In some cases, the locations may be defined on the substrate using some of visual markers (e.g. ink, paint, tape, etc.) For example, the surface of the substrate may be divided up to form the locations. In some cases, the locations may include additional structure such as a pocket, a hook, or other suitable structure for receiving an inventory tag 20, which is described in further detail below. In some cases, each location may be defined by the detection range and/or capability of a detector as also described below.

Each of the locations may have at least one detector 15 associated therewith for detecting a tag received in the location. The detector 15 may be an RFID detector that is operable to read a RFID tag to obtain an identifier associated with that RFID tag.

In some embodiments, each of the locations may have exactly one detector 15 associated therewith. The detector 15 may be configured such that it can only detect the tags 20 that are placed in the location 14 associated with the detector 15. In other words, the detector 15 will not detect other tags 20 that are located in other locations 14 (e.g. adjacent locations or nearby locations). In some embodiments, the detector may detect more than one tag that is placed in the same location. This may allow the tags to "stack" thereby allowing for more tags to be placed at the same location on the same board.

If the detector 15 is an RFID detector (e.g., antenna), the strength of the detector 15 may be selected such that its effective detection range is limited to the location it is associated with such that it will not normally detect the tags 20 that are placed in other locations 14.

In some cases, there may be one detector 15 associated with a plurality of locations 14 such that each detector 15 is able to detect tags placed at the plurality of locations. When one of the tags 20 is received at one or more of the plurality of locations 14, the detector 15 may be operable to determine which of the locations 14 has received the tag. For example, the detector may be a directional RFID detector that is operable to determine which location has received the tag.

In some cases, the inventory station 11 may have detector inhibitors placed at selected locations to limit the detection range of the detectors 15 to the particular location associated with the detector. The detector inhibitors could include metal shielding, Farrday cages, or other components.

Each of the locations 14 generally has an indicator 16 associated therewith. The indicator 16 is selected such that the information provided by the indicator is a simple and intuitive manner. The indicator 16, for example as shown, may be a visual indicator such as a light emitting device (e.g. a LED bulb). The light emitting device may in some cases display a red light (e.g. indicator 16a), an amber light (e.g. indicator 16b), and a green light (e.g. indicator 16c) to indicate various levels of the inventory. In other cases, other colours may be used for the indicator 16. The indicator 16 is not be limited to a visual indicator. In some cases, the indicator 16 may be an audio indicator.

The indicator 16, in some cases, may be LCD display or other display (e.g., OLED, CRT, etc.) which could be used to display characters. In other cases, other suitable forms of indicators may be used.

The inventory system 10 also includes a plurality of tags 20. An exemplary tag 20 will now be described with reference to FIG. 2. The tag 20 may be a RFID tag 20 that contains electronically stored information. The electronically stored information, for example, could be an identifier assigned to the tag. For example, the identifier could be a numeric or alphanumeric number (and which could be unique or non-unique). The tag 20 may also include human readable information such as the identifier in a printed form (as indicated by reference numeral 22) and the name of the item the tag is associated it (as indicated by reference numeral 24). In some cases, the tags may include physical structure that permits the tag to be received at various locations 14 of the inventory station 14.

Figure 2:
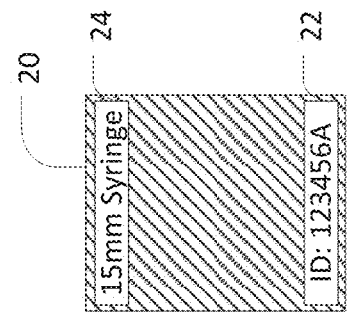
FIG. 2 is a schematic diagram illustrating an exemplary tag that may be received with the inventory station shown in FIG. 1.

Each of the tags 20 is associated with an inventory item type. For example, the tag 20 shown in FIG. 2 is associated with a 15 mm syringe. In some cases each tag may be associated with exactly one inventory item. In some cases, each inventory item may have more than one tag associated therewith. This allows the same inventory item that is being stored at two different locations to have two tags 20 with two different tag identifiers.

In some cases, the tags 20 may be associated with more than one inventory item. For example, if there is more than one type of inventory item stored in a same container, the tag 20 associated with the container may have more than one inventory item type associated therewith.

Generally, the tags 20 are placed at or near the storage locations associated with the inventory item. For example, the tag 20 may be stored on a front surface of a container where the inventory items associated with the tag 20 are stored. In another example, the tag 20 may be stored on a shelf (e.g., in a bin) where the inventory item associated with the tag 20 is stored. Placing the tags 20 near the items allows a user to readily pick up the tag 20 and bring the tag 20 to the inventory station 11 if the user wants to obtain information about the inventory status of the item associated with the tag 20.

For example, the user may be picking up some items from the shelf and notice that the stock for the item seems low. In such cases, the user can pick up the tag 20 associated with the item and bring it to the inventory station 11 to obtain inventory information about the item.

Figure 3:
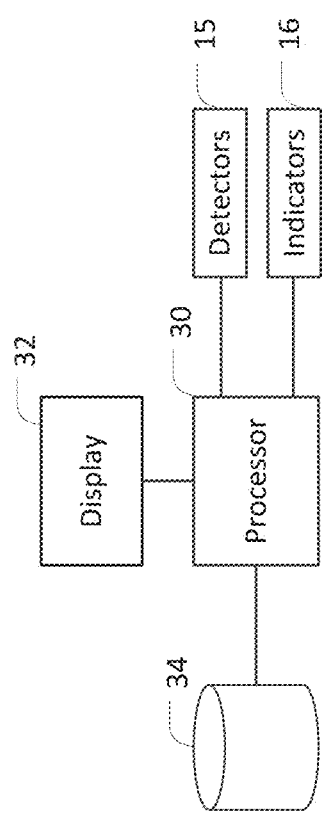
FIG. 3 is a schematic diagram illustrating various components of the inventory system shown in FIG. 1.

Referring now to FIG. 3, illustrated therein is a schematic diagram of some electronic components of the inventory station 11 according to some embodiments. As shown, the inventory station 11 includes a processor 30 coupled to a display/input device (i.e. a touchscreen 32). The processor 30 is also operatively coupled to a data storage device 34, which stores inventory information as described herein below. The processor 30 is also coupled to the detectors 15 and the indicators 16 that are associated with each location where the tag 20 may be received.

Figure 4:
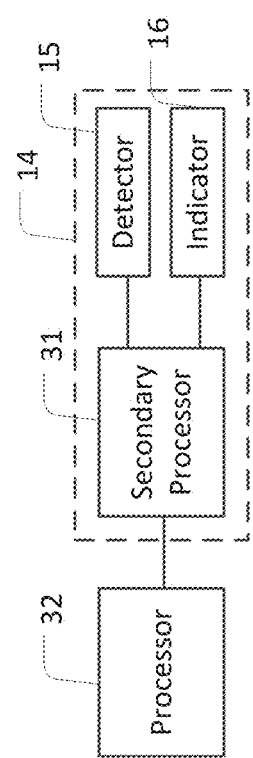
FIG. 4 is a schematic diagram illustrating some components of the inventory station shown in FIG. 1.

In some embodiments, each of the locations may include a secondary processor 31 for controlling the detector 15 and the indicator 16, for example, as shown in FIG. 4. In such cases, the processor 30 may be coupled to the secondary processor 31 and control the operation of the detector and the indicators through the secondary processor 31.

In some cases, the secondary processor 31 may be an integrated circuit or other suitable processor that is configured to operate the detector 15 and the indicator 16 based upon instructions received from the processor 30.

The data storage device 34 stores inventory information about the inventory products. The inventory information may include information about where the products are located, how many products are stored at each location, what is the rate of usage of each product, and other suitable information. It may be possible to determine whether a product should be ordered based upon the quantity remaining and rate of usage of the product. In some cases, the data storage device 34 may be coupled to a server and the processor 30 may communicate with the server to obtain access to the data storage device 34.

In some embodiments, a processor (other than the processor 30) coupled to the data storage device 34 may be configured to determine the current inventory status of each product. In some cases, the products may be back-ordered. That is, an order has been placed for the product, but for one reason or another, the product cannot be delivered until a later date. In some cases, the products may have been ordered and the order is expected to be fulfilled and the shelves restocked. In some cases, the products may need to be ordered.

When a tag 20 is placed at one of the locations 14 on the inventory station 11, the detector 15 detects that a tag has been placed and obtains the tag identifier associated with the tag. The tag identifier is then provided to the processor 30. The processor 30 identifies the current inventory status for the item associated with the identifier.

In some embodiments, the station 11 could be used to receive items into an inventory storage location associated with the station 11. For example, a user may bring products from a different location (e.g., a warehouse) and may use the station 11 to indicate that the products are in the inventory location. In such cases, the user may place the tag associated with the new product at one of the locations 14. The detector 15 then detects the identifier associated with the tag 20. The processor 30 will note that the identifier is either not currently registered and/or that the product associated with the identifier is not currently registered as being in the inventory storage area.

The processor 30 may then proceed to register the product and the identifier as being in the inventory storage location. In some cases, the processor 30 may prompt the user for input or confirmation during the registration process (e.g., using the touchscreen device 32). In some cases, there may be a specific location which is reserved for registering inventory as inventory is added to the storage area. For example, a location immediately to the right of the touchscreen 32, as indicated by reference numeral 14a, could be reserved for receiving inventory products.

In some cases, the processor 30 may communicate with the data storage device 34 to determine the current status of the inventory. For example, the processor 30 may communicate with the server coupled to the data storage device 34 to obtain inventory information associated with the identifier placed at one of the locations 14. The inventory status may be determined based upon based upon the inventory levels and rate of use. In some cases, the inventory status for the inventory item may have been determined previously and the processor 30 is configured to retrieve the predetermined inventory status.

In some embodiments, the processor 30 may be configured to display the inventory information associated with the tag on the touchscreen 32, and activate the indicator 16 associated with the location 14 where the tag was received.

After the inventory status for the item associated with the tag is determined and/or received by the processor 30, the processor 30 may be configured to operate the indicator 16 associated with the location 14 where the tag was placed. For example, the processor may be configured to set the indicator 16 to display a red light, an orange light, or a green light based upon the inventory status of the item. This allows the operator or other individuals who are using the inventory station 11 to obtain, at a glance, inventory status associated with a number of items. Using red, orange, and green lights may also help individuals to inherently understand whether there is a "problem" where some action is necessary.

In some cases, a green light being displayed at the indicator may suggest that no action is necessary, for example, because there is stock of the inventory, or an order for the item has been placed and the order is expected to be delivered in a timely manner (e.g., within the next 24 hours).

In some cases, an orange light may indicate that some action may be desirable. For example, the orange light could suggest that an inventory item has been ordered and received but it has not been restocked on the shelf. In such cases, the inventory item should be restocked on the appropriate shelf before the stock on the shelf runs out.

In some cases, a red light may indicate that immediate action regarding the inventory item is desirable. For example, the red light may indicate that the current inventory level on shelves is below a specified threshold and that immediate or urgent action is required to restock the shelf. In some cases, the red light may suggest that a person follow up with the supplier to expedite shipment.

In some cases, in addition to displaying the orange light and/or the red light, the processor 30 may be configured to place an order automatically or notify an inventory specialist to place the order.

In some embodiments, the processor 30 may be configured to place an order when it is determined that the inventory level is low and that an order has not been placed. This could happen automatically (i.e. without user input) when the tag 20 is received at a location 14.

In some embodiments, the processor 30 may be configured to set the indicator to flash green lights when the processor has determined that the tag 20 at the location 14 should be returned to the inventory storage area.

In some embodiments, the inventory station 11 includes the display device, which in this case is also a touchscreen device 32. The inventory station 11 may also include a user input device, which in the embodiment as shown in FIG. 1 is a touch sensitive input device combined with the display device in the touchscreen 32. In some cases, the touchscreen device 32 may have a processor associated therewith. For example, the touchscreen device 32 may be provided as a commercially available tablet-form computing device such as a tablet computer running Android™ Operating System provided by Google Inc. or an iPad™ sold by Apple Inc. In such cases, the processor 30 may be configured to interface with the processor associated with the touchscreen device to operate the touchscreen device.

The processor 30 may be configured to operate the touchscreen 32 to provide additional information (compared to the visual indicators 16) associated with various inventory items. For example, the processor 30 may provide detailed information about the order, expected delivery times, and so on. The processor 30 may also provide actions that are suggested based upon the tag received. For example, it may suggest that a user restock the inventory, or obtain the inventory from another location within the same institution.

In some cases, the touchscreen 32 may also be used to locate a tag received at the station 11. For example, the inventory station 11 may have received a number of tags 20. It may be time consuming to visually inspect the human readable label on each tag to locate a particular tag. Instead, the user may interact with the touch screen to locate the tags stored thereon. The processor 30 may be configured to flash the indicator light associated with the location where the desired tag is located such that the user is able to identify that tag readily.

In some cases, the station 11 may comprise audio speakers and the processor 30 may be configured to provide audio feedback through the audio speakers.

In some embodiments, the processor 30 may be configured to flash the indicators 16 at locations associated with various tags 20 based upon the filters provided by the user through the input device 32. For example, the user may wish to identify all tags 20 that are located in a particular section of the inventory room. The processor may be configured to flash or blink the indicators at the locations associated with such tags 20. This allows a user to readily identify all of the tags 20 at the inventory station 11 that correspond to the filter that the user has provided.

In some embodiments, the display device 32 and the input device may be used to insert a new inventory item to the system. For example, a user may place a tag 20 with a new identifier (i.e. the identifier associated with the tag is previously unknown to the system) at one of the locations 14. The detector 15 associated with the location 14 detects the new identifier and provide it to the processor 30. The processor 30 will attempt to determine an inventory status associated with the identifier. However, as the identifier is new, the processor 30 will be unable to locate an inventory status associated with the identifier.

In such cases, the processor 30 may prompt the user to input information about the product to be associated with the identifier such that this identifier is associated with a product. In some cases, a tag 20 from another location (i.e. a tag with a previously known identifier) may be imported to the inventory location associated with the inventory station 11.

In some embodiments, the screen 32 may be configured to display a screen saver. The screen saver could include the performance of the system such as number of automatic replenishments, number of stock outs, and so on. In some cases, the system performance information can be used to train various users.

Figure 5:
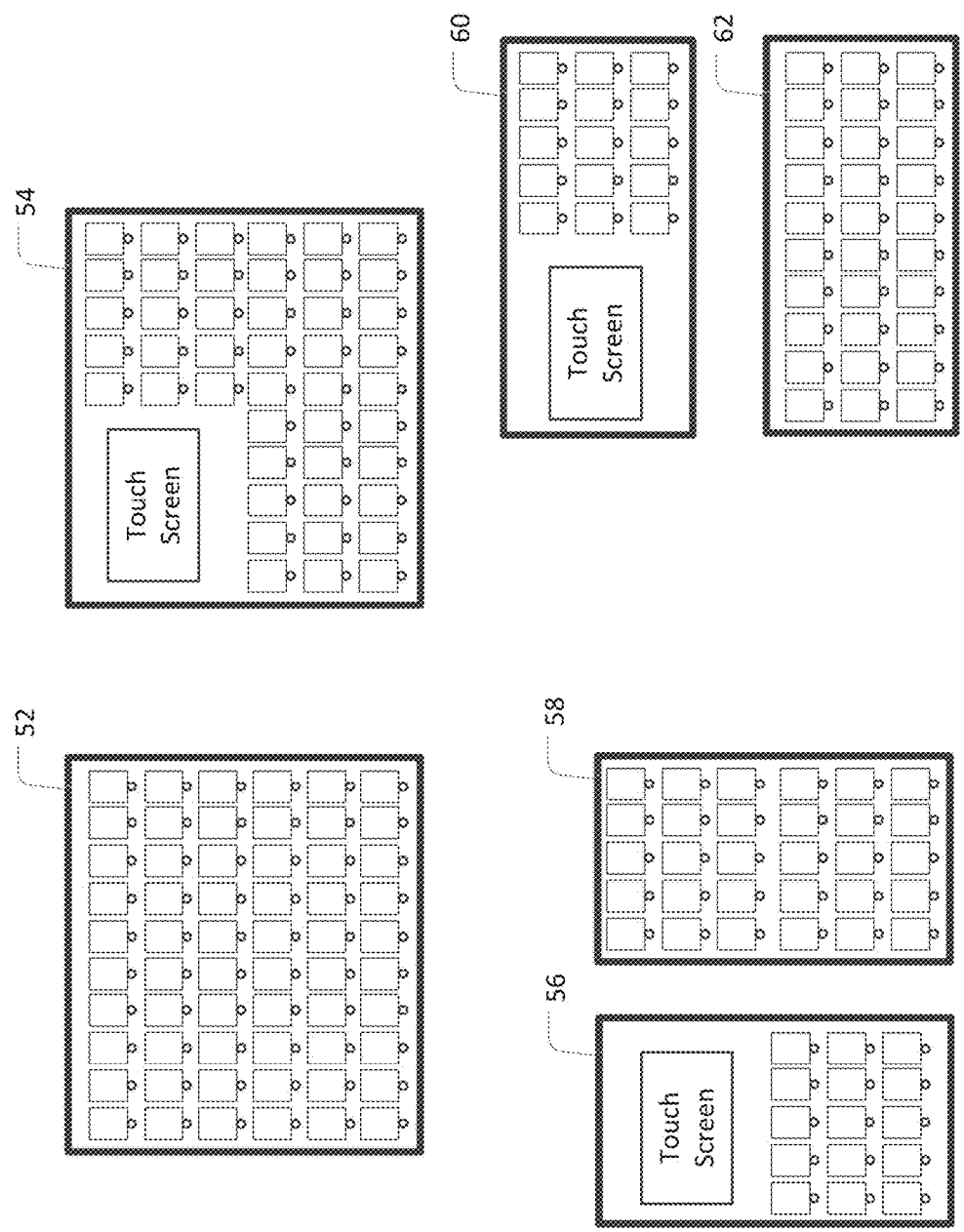
FIG. 5 is a schematic diagram illustrating various inventory stations according to various embodiments.

Referring now to FIG. 5, illustrated therein are other exemplary configurations of the inventory stations, generally indicated by reference numeral 50, according to some embodiments. The inventory stations 50 may be provided with or without a touchscreen display device. The stations without touchscreen display devices may provide more limited functionality as compared to the stations with the display and input devices. However, the stations without display and input devices may be less expensive to manufacture.

In some cases, there may be at least one primary station with a touchscreen at an inventory location that serves as a "master" station, while the other stations (with or without touchscreens) in the location may be configured to act as "slaves" to the station with the touchscreen.

Station 52 features 60 locations in a landscape format (i.e. the width is larger than the height). Station 54 features 45 locations as well as a touchscreen device, also in a landscape format. Station 56 features 15 locations in a portrait format.

The station 58 has a same footprint as the station 56, but features 30 locations as the station 58 does not have a display device. Station 60 features 15 locations and a touchscreen in a landscape format while station 62 features 30 locations without the touchscreen in the same format.

The variety of configurations of the stations that are available demonstrates the customizability of the inventory station that may be possible to suit various operating environments. For instance in larger inventory rooms, a combination of various stations may be installed therein.

In some embodiments, the inventory station 11 may be created by combining one or more substation components, each substation component having a plurality of locations and indicators located thereon. This allows the number of available locations 14 on the inventory station 11 to be modified by adding or subtracting substation components.

Figure 6:
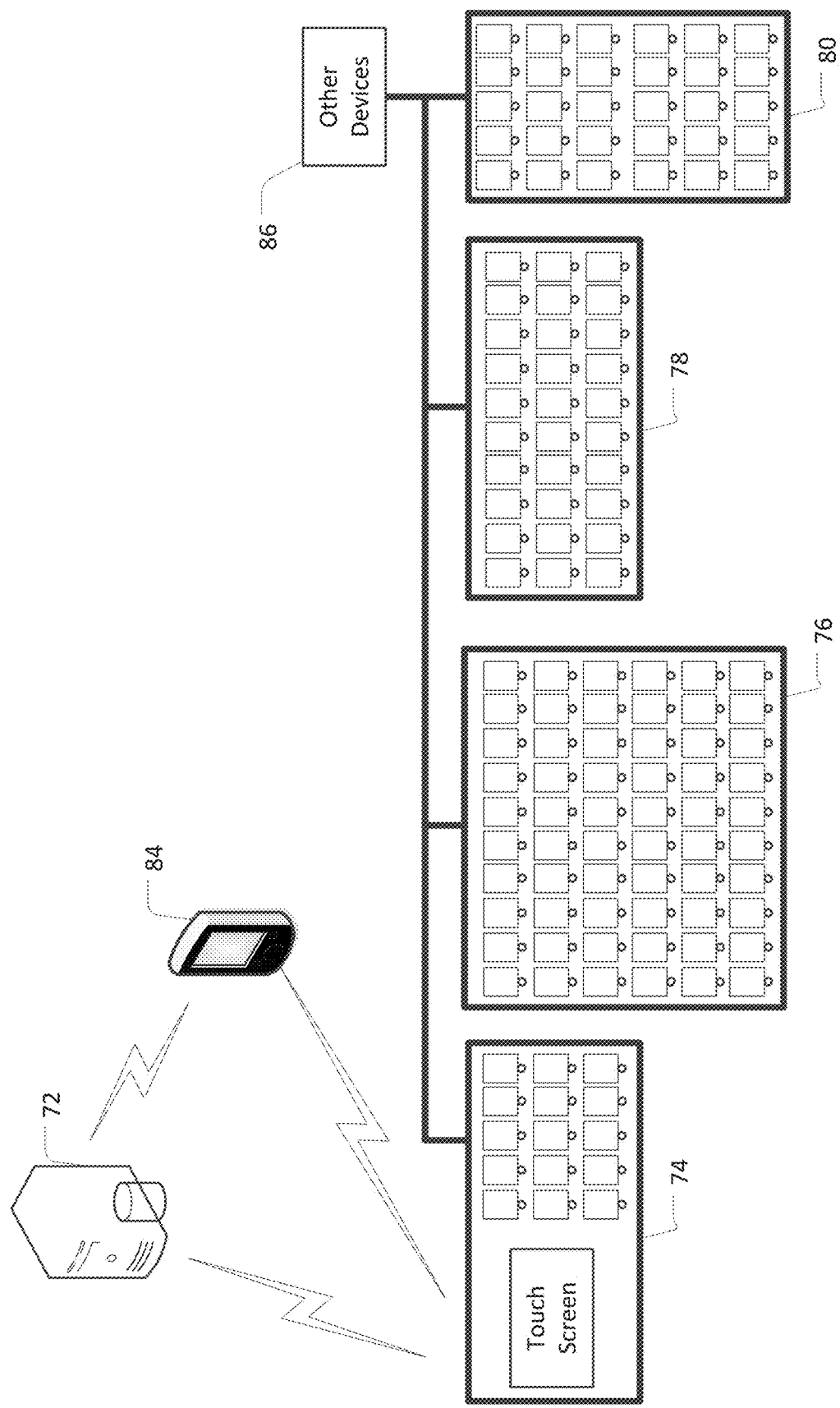
FIG. 6 is a schematic diagram illustrating an inventory system according to some embodiments.

Referring now to FIG. 6, illustrated therein is an inventory system 70 according to some other embodiments. The inventory system 70 features a server 72 which may include a data storage device similar to the data storage device 34 described herein above. The server 72 is in wireless communication with the inventory station 74. The wireless communication may be facilitated by a "WI-FI" (IEEE 802.11 standard compliant) network.

The inventory station 74 is coupled to a number of other inventory stations, namely, stations 76, 78, 80. The inventory station 74 acts as a hub for the other stations and facilitate communication between those stations and the server 72. The station 74 may be coupled to the other stations using a serial communication line. The station 74 may also be coupled other devices, as indicated by reference numeral 82.

The system 70 also includes one or more handheld inventory devices 84, which could be a PDA, a smartphone, a tablet, a laptop, etc. The handheld inventory device 84 may communicate with the server 72 or the inventory station 74 to receive or transmit inventory information.

In some embodiments, the handheld inventory device 84 could cooperate with the system 70 to assist in locating specific tags on an inventory station (e.g., inventory station 74). For example, a user could use the handheld inventory device 84 to request the location of a specific tag (e.g., in order to return that tag to a shelf). Then, on the inventory station 74 the corresponding indicator (e.g., a particular LED) could be activated to indicate the location of that specific tag. In some embodiments, the indicator could be a blinking light, or other visual indicator to draw the user's attention to that specific tag location on the inventory station 74.

Figure 7:
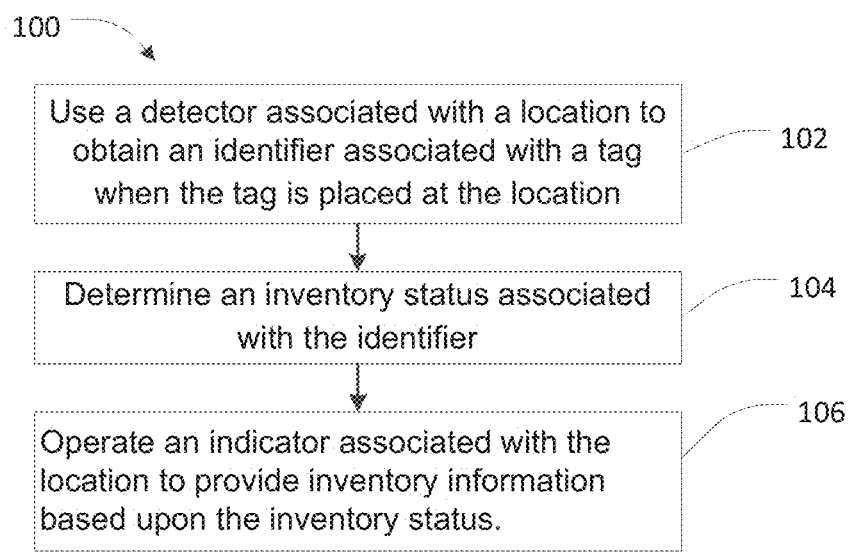
FIG. 7 is a schematic diagram illustrating a method for providing inventory information according to some embodiments.

Referring now to FIG. 7, illustrated therein is a method 100 for providing inventory information according to some embodiments. The method 100 may be implemented using one or more components of the inventory system 10 described herein above. The method 100 begins at step 102.

At step 102, a detector associated with a location is used to obtain an identifier associated with a tag when the tag is placed at the location.

At step 104 an inventory status associated with the identifier is determined.

At step 106, an indicator associated with the location is activated to provide inventory information based upon the inventory status.

Figure 8:
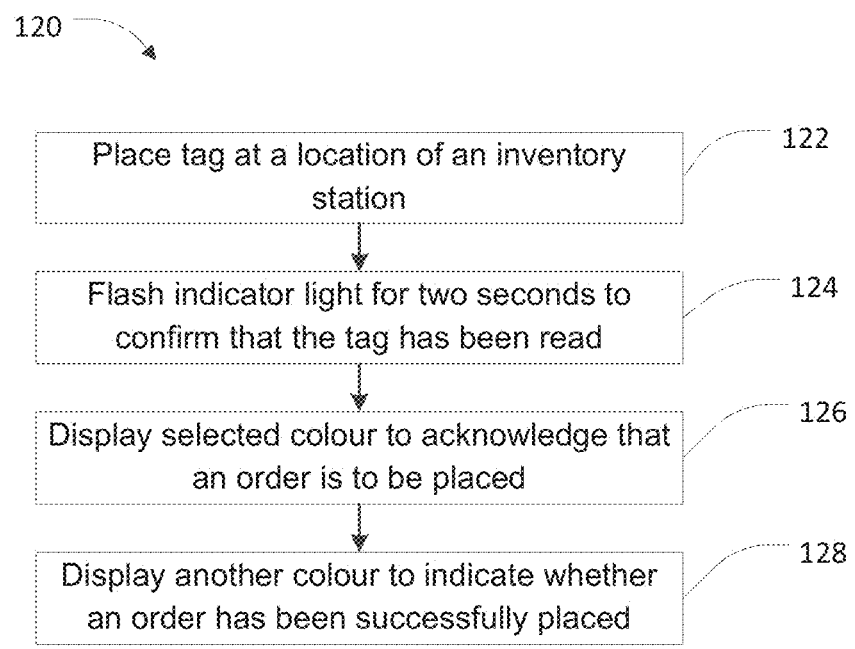
FIG. 8 is a schematic diagram illustrating a method for facilitating ordering of inventory items according to some embodiments.

Referring now to FIG. 8, illustrated therein is a method 120 for ordering inventory items according to some embodiments. The method 120 may be implemented using one or more components of the system 10 as described herein above.

The method 120 begins at step 122, when a tag is placed at a location at an inventory station. The inventory station may be similar to the inventory station 11 described herein above.

At step 124, an indicator light at the location is flashed for two seconds to confirm that the tag has been read.

At step 126, a selected colour (e.g. blue) is displayed at the indicator light to acknowledge that an order is to be placed.

At step 128, another colour is displayed to indicate whether an order has been successfully placed (e.g. green) or whether the item is backordered (e.g. red) and/or further action is necessary.

In some cases, another colour may be displayed after a brief period of time to indicate that the order has been placed and now no further action need be taken by the user.

Using the inventory stations described herein above may provide certain advantages. By having an indicator uniquely associated with each location and each tag when the tag is received allows a user to determine which of the tags requires action. Furthermore, use of a simple visual indicator (such as the red, orange, and green lights) may make it easy for the user to learn the system. The user simply need to place the tags at the locations provided at the inventory stations and determine whether further action is necessary based upon the indicator light.

In some cases, one some users may be trained to act on red lights. For example, nurses or other medical staff may be trained to determine which items (red and/or orange indicators) require his attention by looking at the board and focus his attention on those items. Other users, such as nurses may only be responsible for bringing the tag to a location at the inventory station when they notice that the inventory supply for the item associated with the tag is low.

While the above description provides examples of one or more apparatus, systems and methods, it will be appreciated that other apparatus, systems and methods may be within the scope of the present description as interpreted by one of skill in the art.

The invention claimed is:

1. An inventory information system comprising:
   (a) an inventory station having an array of unique station locations, the inventory station including a substrate and being installed in a vertical position such that it does not take up a large amount of floor space;
   (b) a plurality of indicators, each of the indicators being associated with at least one of the station locations;
   (c) a plurality of tags, each of the tags having an identifier associated therewith and being associated with at least one product, the tags being placed at or near storage locations associated with the at least one product, one or more tags of the plurality of tags being positionable at a station location;
   (d) at least one detector operable to obtain an identifier associated with one of the tags when the tag is positioned at one of the station locations; and
   (e) a processor operatively coupled to the at least one detector and the plurality of indicators, the processor configured to:
      (i) receive an identifier associated with a tag positioned at a station location and to determine an inventory status of at least one product associated with the identifier,
      (ii) operate the indicator associated with the station location of the tag based upon the inventory status to provide information about the inventory status of the at least one product associated with the tag, the indicator being operated to emit a first indicator signal if the inventory status is in a first state and to emit a second indicator signal if the inventory status is in a second state, and
      (iii) determine whether the at least one product should be ordered based upon a quantity remaining and a rate of usage of the at least one product.

2. The system of claim 1, wherein each of the indicators is uniquely associated with one of the station locations.

3. The system of claim 1, wherein at least one of the tags is a RFID tag and wherein the at least one detector comprises at least one radio frequency identification (RFID) detector.

4. The system of claim 3, wherein the at least one RFID detector comprises a plurality of RFID detectors, each of the detectors being associated with each of the station locations and positioned proximate thereto.

5. The system of claim 4, wherein a technical specification of each of the detectors is selected such that tags positioned at station locations other than the station location associated with that detector are not detected by that detector.

6. The system of claim 4, further comprising detection inhibitors that prevent the detectors from detecting tags positioned at station locations other than the station location associated with the detector.

7. The system of claim 1, wherein the at least one detector comprises at least one directional RFID indicator associated with a plurality of station locations, the directional detector operable to detect at least one of the tags positioned at one of the associated station locations and determine which of the associated station locations that the tag is positioned at.

8. The system of claim 1, wherein at least one of the indicators comprises a visual indicator comprising a light emitting device operable to emit different color lights, each of the colors of the light being associated with a particular inventory status; and wherein the processor is configured to operate the indicator to emit the first indicator signal as a light of a first color if the inventory status is in the first state and to emit the second indicator signal as a light of a second color if the inventory status is in the second state.

9. The system of claim 1, wherein at least one of the indicators comprises an audio indicator.

10. The system of claim 1, further comprising at least one display coupled to the at least one processor, the at least one processor configured to provide inventory information using the at least one display.

11. The system of claim 1, further comprising at least one communication device coupled to the at least one processor, the at least one communication device operable to communicate with at least one other processor that is remote from the at least one processor to provide and receive inventory information.

12. The system of claim 1, wherein the first state of the inventory status corresponds to there being stock of the at least one product or an order for the at least one product being placed and wherein the second state of the inventory status corresponds to the current inventory of the at least one product being below a predetermined threshold.

13. A method for providing inventory information, the method comprising:
(a) providing a plurality of tags, each of the tags having an identifier associated therewith and being associated with at least one product, the tags being placed at or near storage locations associated with the at least one product;
(b) providing an inventory station having an array of unique station locations, the inventory station including a substrate and being installed in a vertical position such that it does not take up a large amount of floor space;
(c) using a detector associated with one of the station locations to obtain an identifier associated with at least one tag when the tag is positioned at the station location;
(d) determining an inventory status associated with the identifier for the at least one product;
(e) activating an indicator associated with the station location to provide inventory information based upon the inventory status, the indicator being operated to emit a first indicator signal if the inventory status is in a first state and to emit a second indicator signal if the inventory status is in a second state; and
(f) determining whether the at least one product should be ordered based upon a quantity remaining and a rate of usage of the at least one product.

14. The method of claim 13 wherein, each of the indicators is uniquely associated with each of the station locations.

15. The method of claim 13, wherein at least one of the tags is a RFID tag and wherein the at least one detector comprises at least one radio frequency identification (RFID) detector.

16. The method of claim 15, wherein the at least one RFID detector comprises a plurality of RFID detectors, each of the detectors being associated with one of the station locations and positioned proximate thereto.

17. The method of claim 13, wherein each of the detectors is configured such that tags positioned at station locations other than the station location associated with the detector are not detected.

18. The method of claim 13, further comprising detection inhibitors arranged to inhibit the detectors from detecting tags positioned at station locations other than the station location associated with the detector.

19. The method of claim 13, wherein the at least one detector comprises at least one directional RFID indicator associated with a plurality of station locations, the directional detector operable to detect at least one of the tags positioned at one of the associated station locations and determine which of the associated station locations that the tag is positioned at.

20. The method of claim 13, wherein at least one of the indicators comprises a visual indicator comprising a light emitting device operable to emit different color lights, each of the colors of the light being associated with a particular inventory status; and wherein the indicator is operated to emit the first indicator signal as a light of a first color if the inventory status is in the first state and to emit the second indicator signal as a light of a second color if the inventory status is in the second state.

21. The method of claim 13, wherein at least one of the indicators comprises an audio indicator.

22. The method of claim 13, further comprising providing inventory information using at least one display.

23. The method of claim 13, wherein the first state of the inventory status corresponds to there being stock of the at least one product or an order for the at least one product being placed and wherein the second state of the inventory status corresponds to the current inventory of the at least one product being below a predetermined threshold.

24. The method of claim 13, wherein determining the inventory status associated with the identifier for the at least one product comprises:
retrieving the inventory information stored at a data storage device in association with the identifier, the inventory information comprising an inventory availability of the at least one product; and
generating the inventory status based on the inventory availability of the at least one product.

25. An inventory information system comprising:
a plurality of tags, each of the tags having an identifier associated therewith and being associated with at least one product, the tags being placed at or near storage locations associated with the at least one product;
a substrate defining an array of unique station locations, each station location of the substrate having an indicator, one or more tags of the plurality of tags being positionable at a station location, the substrate being installed in a vertical position such that it does not take up a large amount of floor space;
at least one detector operable to obtain an identifier associated with one of the tags when the tag is positioned at one of the station locations; and
a processor operatively coupled to the at least one detector and the plurality of indicators, the processor configured to:
receive the identifier associated with a tag positioned at a station location and to determine an inventory status of at least one product associated with the identifier;
operate the indicator at the station location of the tag based upon the inventory status to provide information about the inventory status of the at least one product associated with the tag; and determine whether the at least one product should be ordered based upon a quantity remaining and a rate of usage of the at least one product.

26. The system of claim 25, wherein the substrate is mountable on a wall or shelf.

27. The system of claim 25, wherein the substrate is formed of a material chosen from wood, plastic or metal.

28. The system of claim 25, wherein each station location defined by the substrate comprises at least one of a pocket and a hook for receiving one of the plurality of tags.

29. The system of claim 28, wherein at least one of the tags is a RFID tag and wherein the at least one detector comprises at least one radio frequency identification (RFID) detector.

30. The system of claim 1, wherein the processor is configured to determine an inventory status of the at least one product associated with the identifier by:
   retrieving inventory information stored at a data storage device in association with the identifier, the inventory information comprising an inventory availability of the at least one product; and
   generating the inventory status based at least on the inventory availability of the at least one product.

31. The system of claim 25, wherein the processor is configured to determine the inventory status associated with the identifier for the at least one product by:
   retrieving inventory information stored at a data storage device in association with the identifier, the inventory information comprising an inventory availability of the at least one product; and
   generating the inventory status based on the inventory availability of the at least one product.

* * * * *